(12) United States Patent
Sun et al.

(10) Patent No.: US 11,536,643 B2
(45) Date of Patent: Dec. 27, 2022

(54) METHOD FOR AUTOMATED NON-INVASIVE MEASUREMENT OF SPERM MOTILITY AND MORPHOLOGY AND AUTOMATED SELECTION OF A SPERM WITH HIGH DNA INTEGRITY

(71) Applicant: THE GOVERNING COUNCIL OF THE UNIVERSITY OF TORONTO, Toronto (CA)

(72) Inventors: Yu Sun, Toronto (CA); Changsheng Dai, Toronto (CA); Zhuoran Zhang, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 0 days.

(21) Appl. No.: 17/057,504

(22) PCT Filed: May 21, 2019

(86) PCT No.: PCT/CA2019/050690
§ 371 (c)(1),
(2) Date: Nov. 20, 2020

(87) PCT Pub. No.: WO2019/222839
PCT Pub. Date: Nov. 28, 2019

(65) Prior Publication Data
US 2021/0270717 A1    Sep. 2, 2021

(30) Foreign Application Priority Data
May 21, 2018   (GB) ..................................... 1808312

(51) Int. Cl.
*G01N 15/14*   (2006.01)
*C12N 5/071*   (2010.01)
(Continued)

(52) U.S. Cl.
CPC ....... *G01N 15/1429* (2013.01); *C12N 5/0612* (2013.01); *G01N 15/1475* (2013.01);
(Continued)

(58) Field of Classification Search
CPC ............... G01N 15/1429; G01N 15/10; G01N 15/1475; G01N 2015/1075;
(Continued)

(56) References Cited

U.S. PATENT DOCUMENTS 5,744,366 A * 4/1998 Kricka ...................... B01L 7/52
                                                              436/63
7,139,415 B2  11/2006 Finkbeiner
(Continued)

OTHER PUBLICATIONS

International Search Report and Written Opinion issued in International Patent Application No. PCT/CA2019050690 dated Jul. 23, 2021 (12 pages).
(Continued)

*Primary Examiner* — Eileen M Adams
(74) *Attorney, Agent, or Firm* — Dorsey & Whitney LLP

(57) ABSTRACT

A method of automated measurement of motility and morphology parameters of the same single motile sperm. Automated motility and morphology measurements of the same single sperm are performed under different microscope magnifications. The same single motile sperm is automatically positioned and kept inside microscope field of view and in focus after magnification switch. A method of automated non-invasive measurement of sperm morphology parameters under high magnification of imaging. Sperm morphology parameters including subcellular structures are automatically measured without invasive sample staining. A method of automatically selecting sperms with normal motility and morphology and DNA integrity for infertility treatment.

20 Claims, 10 Drawing Sheets

(51) Int. Cl.
    *G02B 21/02* (2006.01)
    *G02B 21/24* (2006.01)
    *G02B 21/26* (2006.01)
    *G02B 21/36* (2006.01)
    *G06T 7/00* (2017.01)
    *G01N 15/10* (2006.01)

(52) U.S. Cl.
    CPC ......... *G02B 21/025* (2013.01); *G02B 21/241* (2013.01); *G02B 21/26* (2013.01); *G02B 21/367* (2013.01); *G06T 7/0014* (2013.01); *G01N 2015/1006* (2013.01); *G01N 2015/1075* (2013.01); *G01N 2015/1497* (2013.01); *G06T 2207/10056* (2013.01); *G06T 2207/20036* (2013.01); *G06T 2207/20061* (2013.01); *G06T 2207/30024* (2013.01)

(58) Field of Classification Search
    CPC ... G01N 2015/1497; G01N 2015/1006; G02B 21/241; G02B 21/025; G02B 21/26; G02B 21/367; G06T 7/0014; G06T 2207/20061; G06T 2207/30024; G06T 2207/10056; G06T 2207/20036; C12N 5/061; C12N 5/0612; G06V 10/245; G06V 20/698
    See application file for complete search history.

(56) References Cited

U.S. PATENT DOCUMENTS

2006/0133657 A1  6/2006  Schmid et al.
2013/0143200 A1* 6/2013  Sun ................. C12M 23/22
                                         435/303.1
2018/0246028 A1* 8/2018  Hsu ................ G01N 15/1434

OTHER PUBLICATIONS

Rijsselaere et al., "Automated sperm morphometry and morphology analysis of canine semen by the Hamilton-Thorne analyser", Theriogenology, 2004, 62(7): 1292-1306 (Abstract).

Changsheng Dai et al., "Automated Non-Invasive Measurement of Single Sperm's Motility and Morphology", IEEE Transactions on Medical Imaging, 2018, 37(10): 2257-2265.

Zhuoran Zhang, Ph.D. et al., "Quantitative selection of single human sperm with high DNA integrity for intracytoplasmic sperm injection" Fertil Steril, 2021, 116(5): 1308-1318.

* cited by examiner

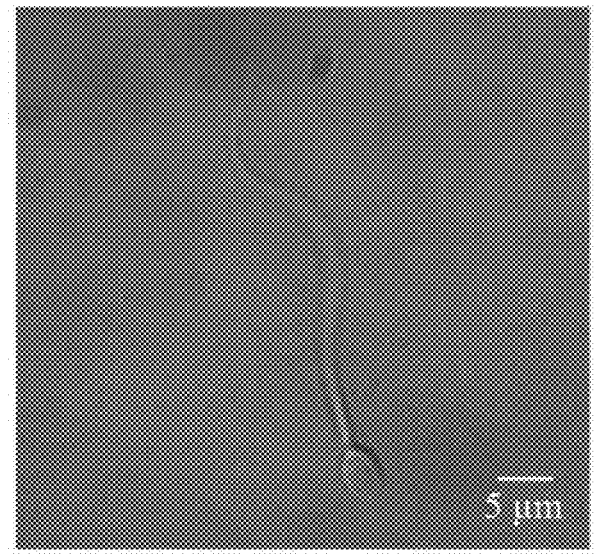
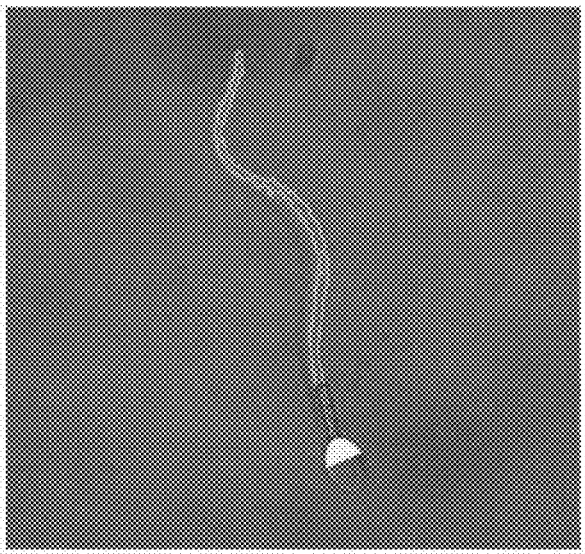
FIG. 9A　　　　　　　　　　　　　　FIG. 9B
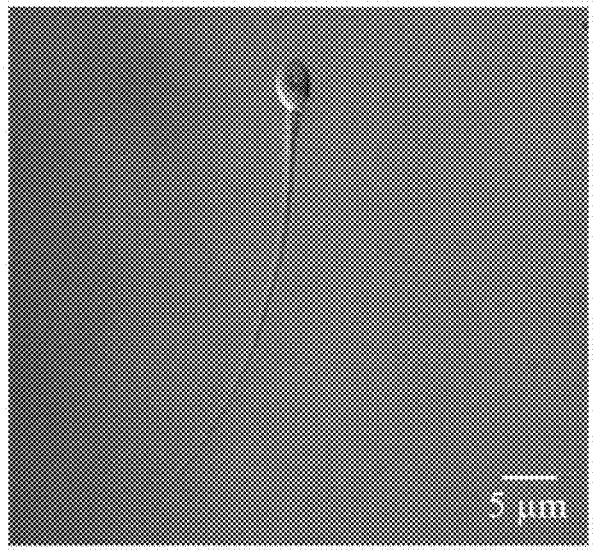
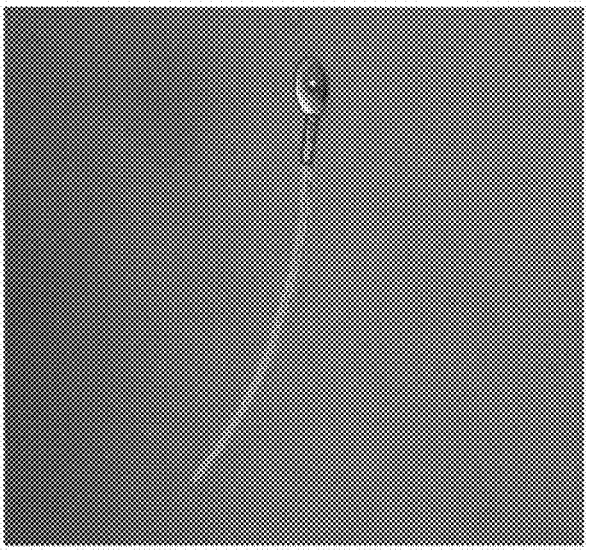
FIG. 10A　　　　　　　　　　　　　FIG. 10B ced sperm for
METHOD FOR AUTOMATED NON-INVASIVE MEASUREMENT OF SPERM MOTILITY AND MORPHOLOGY AND AUTOMATED SELECTION OF A SPERM WITH HIGH DNA INTEGRITY

CROSS-REFERENCE TO RELATED APPLICATIONS

This application is a national stage application under 35 U.S.C. § 371 of International Application No. PCT/CA2019/050690 filed 21 May 2019 entitled "A method for automated non-invasive measurement of sperm motility and morphology and automated selection of a sperm with high DNA integrity," which claims priority to United Kingdom Patent Application No. 1808312.1 filed 21 May 2018, and the contents of each are hereby incorporated herein in their entirety by reference for all purposes.

FIELD

The invention relates to methods for automated motility and morphology measurement of the same single motile sperm under different microscope magnifications and automated selection of sperms with normal motility and morphology.

BACKGROUND

The World Health Organization (WHO) reports that 48.5 million couples worldwide experience infertility, and many of these couples seek in vitro fertilization (IVF) for treatments. There are presently approximately 3,000 IVF clinics worldwide, with 458 clinics in the U.S. alone, and the number is growing rapidly. Measurement of sperm motility and morphology is important for IVF, with wide applications such as male infertility diagnosis and selecting the sperm for IVF treatment such as intracytoplasmic sperm injection (ICSI).

Due to a sperm's fast movement (e.g., >25 µm/s), a sperm can quickly move out of the microscope field of view. Hence, sperm motility measurement requires a large microscope field of view to observe sperm trajectories, corresponding to a low microscope magnification such as 20×.

Sperm morphology measurement requires high spatial resolution and high microscope magnification to visualize subcellular structures such as vacuoles on the sperm head. Visualizing vacuoles is important because vacuoles originate from the abnormal condensation of chromatins, indicating fragmented or damaged sperm DNA. However, vacuoles can only be visible under a high microscope magnification. Although certain morphology parameters such as the size of the sperm head can be estimated under low microscope magnification (e.g., 20×), a high microscope magnification of 100× is required for accurate measurement of sperm morphology.

Presently in IVF clinics, a human operator (an embryologist) estimates, rather than quantitatively measures, sperm motility under low microscope magnification, by looking into the eyepieces of a microscope. After a sperm of interest is identified, the human operator switches to high microscope magnification. However, microscope magnification switching changes the field of view, and the sperm is also moving during magnification switch. Thus, it is highly challenging, if not impossible, to relocate and to follow the same sperm after switching to a high microscope magnification (e.g., from 20× to 100×).

Intracytoplasmic sperm injection (ICSI) is used in more than 70% of all IVF treatments. Fertilization created by ICSI involves the insertion of a single sperm into an oocyte with a sharp micropipette. The embryologist selects a sperm for ICSI based on qualitative observation of the motility and morphology of the sperm, which involves great subjectivity and inconsistency. Sperm selection for ICSI demands an automated technique for measuring motility and morphology parameters on the same single sperm and repeating such measurements on multiple sperms for comparing which sperm to select for ICSI. Also, quantitative criteria to select normal sperms based on their motility and morphology are required for sperm selection in IVF treatment.

Commercial computer aided sperm analysis (CASA) instruments are used in IVF clinics for sperm motility and morphology measurement. In CASA, a portion of semen sample is first used for motility measurement under low microscope magnification, then another portion of semen sample is killed and stained for morphology measurement under high magnification. See U.S. Pat. No. 8,390,681B1 for an example. The staining process makes CASA an invasive technique, making the measured sperm unusable for subsequent IVF treatment such as ICSI. Also importantly, CASA fails to address the demand of measuring the same sperm's motility and morphology parameters. Since morphology measurement is performed on another population of sperm, CASA systems do not and are incapable of relocating the same single sperm under different microscope magnifications.

U.S. Pat. Appl. Publ. No. 20070298454A1 and WO 2005/080944A1 disclosed a method for measurement of motility and morphology of the same individual sperm. However, both measurements are performed under a fixed microscope magnification. It did not disclose morphology measurement of subcellular sperm structures under high microscope magnification. Automated switching of microscope magnification for performing motility and morphology measurement on the same single sperm was also not disclosed.

U.S. Pat. No. 6,929,945B2, U.S. Pat. No. 7,807,452B2, U.S. Pat. No. 6,426,213B1 and U.S. Pat. No. 5,866,354A disclosed various microchannel devices for estimating sperm motility and sorting motile sperms. The number of motile sperm that can migrate through the microchannels is counted. Motility parameters of individual sperms, however, cannot be determined by these devices. Our invention does not use any of these microchannel devices.

US. Pat. Appl. Publ. No. 20120148141A1 disclosed a lens-free holographic system for semen analysis. Holograms of sperm are used to reconstruct sperm trajectories and determine sperm motility. Morphology measurement was not disclosed. In addition, the holographic system has a fixed magnification and does not switch magnifications. Our invention does not use this holographic system.

U.S. Pat. Appl. Publ. No. 20060133657A1 disclosed a microscopy system with automated magnification switch for examining immotile biological cells. The system cannot compensate for the motion of a motile cell such as a sperm during magnification switch such that the motile cell will be lost in the microscope field of view after switching to high magnification.

U.S. Pat. Appl. Publ. No. 2012002823A2, and U.S. Pat. No. 9,157,063B2, and U.S. Pat. No. 5,135,759A disclosed methods for sex selection of sperms. Binding agents, pH, or fluorescent dye were used to separate sperms bearing X or Y chromosomes. Our invention does not select sperms for sex selection and does no use binding agents, pH or fluorescent dye for sperm selection.

U.S. Pat. Appl. Publ. No. 20130143200 A1, C. Leung, et al. (IEEE Trans. Biomedical Engineering, Vol. 58, pp. 935-942, 2011), Z. Lu, et al. (IEEE Trans. Biomedical Engineering, Vol. 58, pp. 2102-2108, 2011), and J. Liu, et al. (IEEE Trans. Biomedical Engineering, Vol. 60, pp. 390-396, 2013.) disclosed methods for automated tracking and manipulation of motile sperm specimen. A single sperm is automatically tracked, and with a micropipette, is immobilized, aspirated and injected into an oocyte for in vitro fertilization. The tracked position of the sperm head is determined by calculating the centroid of the sperm head contour, which is common practice as reported in literature and is also adopted in the present invention. To deal with the challenges of tracking multiple sperms under interference (sperms crossing over each other and swimming in close proximity), these previous methods used the direction vector (time-averaged swimming direction of a sperm) to distinguishing sperms under interference, and did not use head orientation and head shape instead of the direction vector for distinguishing interfering sperms. In these documents, a target sperm to be manipulated was selected manually or automatically, in which automated sperm selection was based on sperm motility measurement only without using sperm morphology information. Methods for sperm morphology measurement were not disclosed either in our previous work. Furthermore, the tracking and manipulation of sperm were performed under the same microscope magnification; and automated switching of microscope magnification for performing motility and morphology measurement on the same sperm was not disclosed.

SUMMARY

Achieving automated non-invasive measurement of the same single sperm's motility and morphology and selection of sperms with normal motility and morphology require: (1) a microscopy system that is equipped with a motorized nosepiece and integrates motorized positioning devices for sperm positioning and auto-focusing; (2) methods for relocating the same single motile sperm after switching magnifications; (3) computer vision algorithms for measuring sperm motility and morphology parameters under different magnifications; (4) quantitative criteria of determining normal motility and morphology for a single sperm.

In one embodiment the present invention provides for a method of automatically quantifying motility and morphology parameters of the same single motile sperm characterized in that said method comprises the following steps: (a) acquiring low magnification microscopic images of multiple sperms and automatically tracking each sperm to determine each sperm's motility parameters; (b) automatically switching to high magnification and automatically positioning the single motile sperm of interest, identified under low magnification, inside microscope field of view and automatically re-focusing on the sperm; (c) automatically measuring morphology of the single sperm from acquired high magnification microscopic images.

In another embodiment the present invention provides for a method of automated non-invasive measurement of sperm morphology under high magnification, said method comprising: (a) automatically identifying and separating the sperm head, midpiece and tail in images; (b) automatically measuring sperm head parameters such as acrosome area and nucleus area and detecting vacuoles on the sperm head; (c) automatically measuring sperm midpiece parameters; (d) automatically measuring sperm tail parameters and detecting tail abnormality.

In another embodiment the present invention provides for a method of quantitative automated selection of sperms with normal motility and morphology for infertility treatment, said method comprising: (a) automatically choosing a candidate sperm with high motility via motility measurement under low magnification; (b) automatically positioning the same sperm inside field of view after switching to high magnification; (c) automatically measuring the sperm's morphology parameters; (d) repeating the steps before on multiple candidate sperms and automatically selecting a normal sperm in terms of both motility and morphology.

In one embodiment, the present invention provides for a computer implemented method of automatically quantifying motility and morphology parameters of a single motile microscopic specimen in a population of motile specimens using a computer, characterized in that said method comprises the following steps: (a) placing, or enabling the placement of, the population of motile microscopic specimens on a stage of a microscope means, the microscope means having (i) a motorized positioner controlling the motion of the stage, (ii) a motorized objective nosepiece, (iii) a first microscope magnification objective and a second magnification objective mounted on the motorized objective nosepiece, the second magnification objective having a higher magnification power than the first magnification objective, (iv) an image acquiring unit mounted on the microscope means, and (v) a focus adjusting motor, the motorized positioner, motorized objective nosepiece, the image acquiring unit and the focus adjusting motor being operationally connected to the computer; (b) automatically obtaining images of the population of motile microscopic specimens using the image acquiring unit through the first microscope magnification objective; (c) automatically moving the motorized positioner for tracking a plurality of motile microscopic specimens in the population based on the images taken through the first microscope magnification objective to quantify the motility parameters of the tracked motile microscopic specimens; (d) selecting a single motile microscopic specimen using the quantified motility parameters; (e) automatically (i) switching to a second magnification objective using the motorized nosepiece, (ii) positioning said selected single motile microscopic specimen inside a field of view of said second magnification objective using the motorized positioner, (iii) re-focusing on the single motile microscopic specimen using the focus adjusting motor, and (iv) obtaining images with the image acquiring unit of the single motile microscopic specimen through the second magnification objective; and (f) quantitatively measuring morphology parameters of said selected single motile microscopic specimen using the microscopic images taken with the second magnification objective.

In one embodiment of the computer implemented method, said automatically positioning is based on a calibrated coordinate transformation and prediction of the selected single motile microscopic specimen position, wherein said calibrated coordinate transformation compensates for a change of field of view and focus after the first magnification objective is switched to the second magnification objective.

In another embodiment of the computer implemented method, the visual tracking is achieved by a joint probabilistic data association filter (JPDAF).

In another embodiment of the computer implemented method, the motile microscopic specimen is a sperm and the joint probabilistic data association filter (JPDAF) is adapted by incorporating a sperm head orientation and morphology features of the sperms to differentiate the tracked individual sperms during crossing over and close proximity of sperms in a population of sperm.

In another embodiment of the computer implemented method, the head orientation is defined as an angle between the major axis of the sperm head and the horizontal axis of the image.

In another embodiment of the computer implemented method, the morphology features include a head shape of the sperm.

In another embodiment of the computer implemented method, the prediction of the single motile microscopic specimen position compensates for the motion of the single motile specimen during magnification switch.

In another embodiment of the computer implemented method, the motile microscopic specimen is sperm, and wherein said prediction of the single sperm position is based on a sperm head position or a sperm tail position measured under the first magnification.

In another embodiment of the computer implemented method, the positioning of said motile specimen is performed continuously under the second magnification objective by tracking and positioning said motile sperm to compensate for the sperm motion after magnification switch.

In another embodiment of the computer implemented method, the motility measurement includes one or more of VCL (curvilinear velocity), VSL (straight-line velocity), VAP (average path velocity), ALH (amplitude of lateral head displacement), LIN (linearity), WOB (wobble), STR (straightness), BCF (beat-across frequency), MAD (mean angular displacement), or a combination thereof.

In another embodiment of the computer implemented method of the present invention, the method further comprises repeating steps (a) to (c) for other motile microscopic specimens in the population, and wherein the method further comprises selecting a candidate motile microscopic specimen based on a quantitative comparison amongst the selected motile microscopic specimens in measured motility and measured morphological parameters.

In another embodiment of the computer implemented method, the selection of the candidate motile microscopic specimen is achieved by finding motile microscopic specimen with measured motility and morphology parameters meeting a predetermined quantitative criteria of motility and morphology.

In another embodiment of the computer implemented method, the predetermined quantitative criteria of motility and morphology are determined by finding a range of motility and morphological parameters which indicate high DNA integrity of the motile microscopic specimen.

In another embodiment of the computer implemented method of the present invention, the motile microscopic specimen is sperm, and wherein said predetermined quantitative criteria of motility include a curvilinear velocity (VCL) equal or greater than 20 μm/s, linearity (LIN) higher than 0.9, and said predetermined quantitative criteria of morphology include a sperm head length-width ratio between 1.5 to 1.75, without vacuole. In aspects of this embodiment, the predetermined quantitative criteria of morphology can further include a sperm without midpiece abnormality, or a sperm without tail abnormality and without midpiece abnormality, or a sperm without tail abnormality. In aspects of this embodiment the VCL is equal or greater than 25 μm/s.

In another embodiment of the computer implemented method of the present invention, the motile microscopic specimen is sperm, and wherein said predetermined quantitative criteria of motility and morphology are a straight-line velocity (VSL) equal or greater than 10 μm/s, and a head having length-width ratio between 1.5 to 1.75, without vacuole. In aspects of this embodiment, the predetermined quantitative criteria of morphology can further include a sperm without midpiece abnormality, or a sperm without tail abnormality and without midpiece abnormality, or a sperm without tail abnormality. In aspects of this embodiment, the VSL is equal or greater than 20 μm/s.

In another embodiment of the computer implemented method, the motile microscopic specimen is sperm, and wherein said predetermined quantitative criteria of motility and morphology include a normal motility and a normal head morphology.

In another embodiment of the computer implemented method, the motile microscopic specimen is sperm, and wherein said predetermined quantitative criteria of motility and morphology include a normal motility, a normal sperm's head morphology and a normal sperm's midpiece.

In another embodiment of the computer implemented method, the motile microscopic specimen is sperm, and wherein said predetermined quantitative criteria of motility and morphology include a normal motility, a normal sperm's head morphology and a normal sperm's tail.

In another embodiment of the computer implemented method, the motile microscopic specimen is sperm, and wherein said predetermined quantitative criteria of motility and morphology include a normal motility, a normal sperm's head morphology, a normal sperm's midpiece and a normal sperm's tail.

In another embodiment of the computer implemented method of the present invention, predetermined quantitative criteria of both motility and morphology must be met at the same time, for selecting a sperm with high probability of DNA integrity.

In another embodiment, the present invention provides for a method for automated non-invasive measurement of a morphological feature or features of a live, unstained motile microscopic specimen, comprising: (a) automatically segmenting the morphological feature or features of the motile microscopic specimen under a microscope, and (b) automatically measuring the morphological feature or features under the microscope.

In one embodiment of the method for automated non-invasive measurement of a morphological feature of a live, unstained motile microscopic specimen of the present invention, step (a) includes automatically segmenting at least two morphological features, or automatically segmenting at least three morphological features of the motile microscopic specimen under the microscope.

In one embodiment of the method for automated non-invasive measurement of a morphological feature of a live, unstained motile microscopic specimen of the present invention, the motile specimen is sperm, and the sperm morphological feature or features include one or more of the sperm's head, midpiece and tail, and wherein the sperm morphological feature or features are separated in an image by measuring width differences of the head, the midpiece and the tail.

In one embodiment of the method for automated non-invasive measurement of a morphological feature of a live, unstained motile microscopic specimen of the present invention, the width is measured by quantifying a distance from points on a contour of the sperm to a centerline of the sperm.

In one embodiment of the method for automated non-invasive measurement of a morphological feature of a live, unstained motile microscopic specimen of the present invention, the centerline is obtained by iterative image thinning.

In one embodiment of the method for automated non-invasive measurement of a morphological feature of a live, unstained motile microscopic specimen of the present invention, the morphological feature is the sperm's head, and wherein said measurements include the head size and shape, acrosome area, nucleus area, vacuole number, vacuole area, and wherein said acrosome area and nucleus area are measured under a high magnification objective by detecting regions with different pixel intensities on the sperm head, and wherein said vacuole number and vacuole area are detected by detecting holes on the sperm head in binarized high magnification images.

In one embodiment of the method for automated non-invasive measurement of a morphological feature of a live, unstained motile microscopic specimen of the present invention, the detecting the holes is achieved by using a Hough transform or template matching.

In one embodiment of the method for automated non-invasive measurement of a morphological feature of a live, unstained motile microscopic specimen of the present invention, the morphological feature is the sperm's midpiece, and wherein abnormalities in midpiece size and midpiece angle are measured by a minimum bounding box or a convex hull.

In one embodiment of the method for automated non-invasive measurement of a morphological feature of a live, unstained motile microscopic specimen of the present invention, the morphological feature is the sperm's midpiece, and wherein an excess residual cytoplasm on the midpiece is detected by inspecting abnormal width of the midpiece.

In one embodiment of the method for automated non-invasive measurement of a morphological feature of a live, unstained motile microscopic specimen of the present invention, the morphological feature is the tail, and wherein: (a) an abnormality in tail coiling is automatically detected by detecting closed contours on the sperm tail; (b) an abnormality in tail bending is automatically detected by detecting a sharp turn in a centerline of the sperm tail; and (c) an abnormality of tail width non-uniformity is automatically detected by measuring a distribution of a distance from points along the tail's contour to a centerline of the sperm tail.

In another embodiment, the present invention provides for a computer program comprising instructions, which, when the program is executed by a computer, cause the computer to carry out the method of the previous embodiments.

In another embodiment, the present invention provides for a system comprising: (a) a host computer; (b) a microscope; (c) a motorized positioner, which controls a motion of a container for containing motile microscopic specimens, the motorized positioner being operationally connected or linked through wire connection or wireless connection to the host computer; (d) at least a first objective magnification lens and a second objective magnification lens, the second objective magnification lens having a greater magnification power than the first objective magnification lens, the first and second magnification lenses being mounted on a motorized objective nosepiece; (e) a motorized objective nosepiece, which controls a switch of first and second objectives magnification lenses with different magnifications, and is operationally connected or linked or linked through wire connection or wireless connection to the host computer; (f) an image acquiring unit mounted on the microscope (2) operationally connected or linked through wire connection or wireless connection to the host computer; and (g) a focus adjusting motor, which may be mounted on a focus adjusting knob of the microscope and be operationally connected or linked through wire connection or wireless connection to the host computer; wherein the host computer comprises a computer program comprising instructions to execute the steps of the method according to any one of the above embodiments.

BRIEF DESCRIPTION OF THE DRAWINGS

A detailed description of one or more embodiments is provided herein below by way of example only and with reference to the following drawings, in which:

FIGS. 9A and 9B show a sample image illustrating the separation of sperm head, midpiece and tail, and the detection of nucleus region under high magnification.

FIGS. 10A and 10B show a sample image illustrating the separation of sperm head, midpiece and tail, and the detection of a vacuole on the sperm head under high magnification.

DETAILED DESCRIPTION OF THE INVENTION

Definitions

Figure 1:
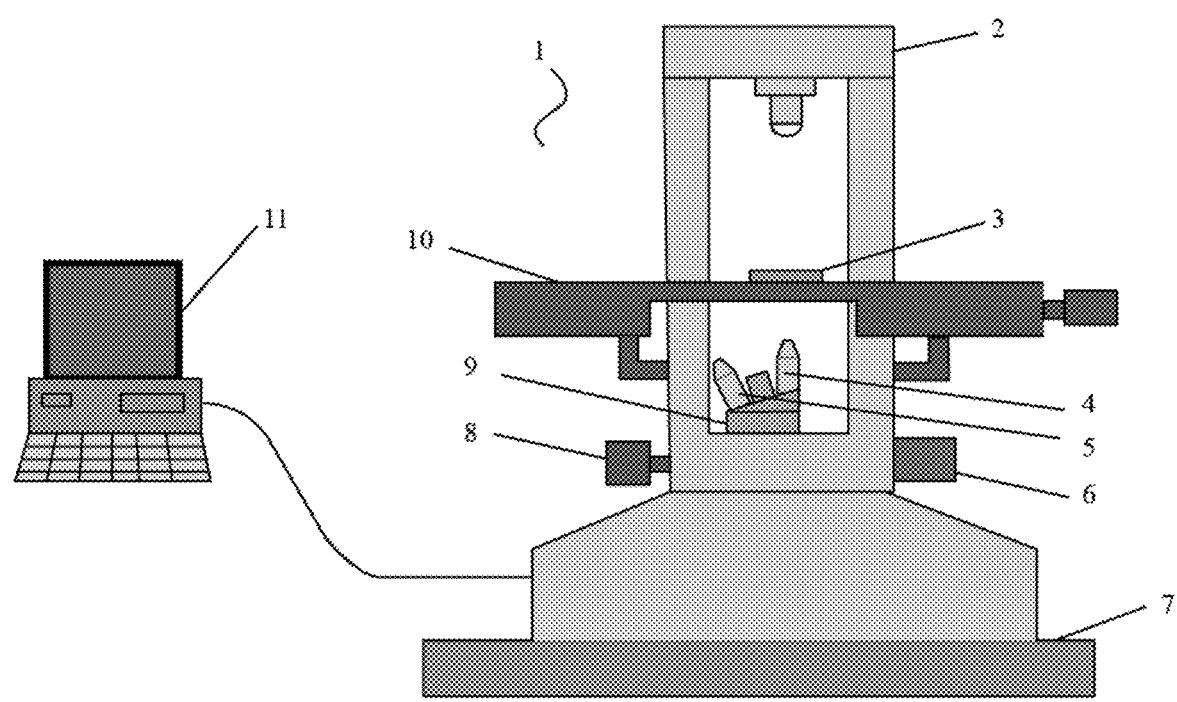
FIG. 1 illustrates a schematic view of the system for automatically quantifying motility and morphology parameters of the same single motile sperm in accordance to one embodiment of the present invention.

The following definitions, unless otherwise stated, apply to all aspects and embodiments of the present application.

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "include without limitation"). Singular forms included in the claims such as "a", "an" and "the" include the plural reference unless expressly stated otherwise. All relevant reference, including patents, patent applications, government publications, government regulations, and academic literature are hereinafter detailed and incorporated by reference in their entireties.

The terms "population" or "plurality," as used herein, is defined as two or more than two. The term "another," as used herein, is defined as at least a second or more. The phrase "at least one of . . . and . . . " as used herein refers to and encompasses any and all possible combinations of one or more of the associated listed items. As an example, the phrase "at least one of A, B and C" includes A only, B only, C only, or any combination thereof (e.g. AB, AC, BC or ABC). The term "substantially" includes exactly the term it modifies and slight variations therefrom.

The term "about" modifying any amount refers to the variation in that amount encountered in real world conditions of producing materials such as polymers or composite materials, e.g., in the lab, pilot plant, or production facility. For example, an amount of an ingredient employed in a mixture when modified by about includes the variation and degree of care typically employed in measuring in a plant or lab and the variation inherent in the analytical method. Whether or not modified by about, the amounts include equivalents to those amounts. Any quantity stated herein and modified by "about" can also be employed in the present invention as the amount not modified by about.

"Automatic/automated/automatically" as used in this document means that the methods of the present invention, including the steps of quantification of motility and morphology, are free of human operator control (for example manual and/or joy-stick based control) or where human intervention is limited to entering input data and/or pressing a start operation.

The term "low magnification" or "first magnification" refers to a magnifying power of a microscope's objective lens sufficient to track a motile microscopic specimen. The term "high magnification" or "second magnification" refers to magnifications higher than the low magnification. The term "high magnification" refers a magnifying power of a microscope's objective sufficient to study the structural features or parts, or perform morphological measurements of a microscopic specimen. For example, if the first magnification is 20×, then the second magnification would be a magnification that is higher than 20× and sufficient to study the structural features or parts, or perform morphological measurements of the microscopic specimen under study. If the first magnification is 40×, then the second magnification would be a magnification power that is higher than 40× and sufficient to study the structural features or parts, or perform morphological measurements of the microscopic specimen under study. Likewise for magnifications of 50×, 60×, 70×, 80×, 100× and so forth.

The term "microscopic specimen" refers to single cells (including single celled microorganisms) or multicellular organisms that cannot be seen with the naked eye with ease. Examples of single cell microscopic specimen include spermatozoa, oocytes, red blood cells, white blood cells, bacteria, eukaryotic unicellular organisms, myxozoa. Examples of multicellular microscopic specimen include microscopic arthropods (examples dust mites, and spider mites); microscopic crustaceans; rotifers; microscopic nematodes. The term "microscopic specimen" also applies to animals at their various stages of embryonic and larval development, such as fish larva, amphibian larva, insect larva and so forth.

The term "motile microscopic specimen" refers to a microscopic specimen having the ability to move independently, as well as to a microscopic specimen that moves due to external forces. Examples of motile microscopic specimen having the ability to move independently include spermatozoa (sperm), as well as unicellular prokaryote and eukaryote microorganisms. Examples of motile microscopic specimen that move dependently (i.e. due to external forces), includes microscopic specimens that are suspended in solution and move because of the natural movement of the solution in which they are suspended.

In computer vision, image segmentation is the process of partitioning a digital image into multiple segments (sets of pixels). The goal of segmentation is to simplify and/or change the representation of an image into something that is more meaningful and easier to analyze. Image segmentation is typically used to locate objects and boundaries (lines, curves, etc.) in images.

Overview

The present invention in one embodiment provides for a method and a system of automated measurement of motility and morphology parameters of the same single microscopic motile specimen. The methods of the present invention can be computer implemented methods using a computer.

According to an embodiment, different from existing methods which perform motility and morphology measurements either on different populations of sperm or under a fixed microscope magnification, the method of the present invention performs motility measurement of a sperm under a first microscope magnification and morphology measurement of that same sperm under a second microscope magnification that is higher than the first microscope magnification for the same single motile microscopic specimen. After magnification switch from the first microscope magnification to the second microscope magnification, the same single motile microscopic specimen is automatically positioned inside microscope field of view of the second microscope magnification and refocused for morphology measurement. In another embodiment, the invention provides for a method of automatically measuring motile microscopic specimen morphology under the second microscope magnification without invasive sample processing such as fixation and staining. Hence, in the case of sperm, the sperm after measurement is usable for in vitro fertilization (IVF) treatment such as intracytoplasmic sperm injection (ICSI). In yet another embodiment, the present invention provides for a method of automated quantitative selection of motile specimen with normal motility and morphology. Different from manual selection in which the human operator/embryologist qualitatively and subjectively estimates sperm parameters, the method uses the motility and morphology parameters that are automatically measured on the same sperm to quantitatively and objectively select normal sperms.

The following description of the present invention uses sperm as an example. However, one skilled in the art understands that the embodiments of the present invention can be used for motile microscopic specimens. As such, the term "motile microscopic sperm" in the description below, can be replaced with the term "motile microscopic specimen."

The System

FIG. 1 shows a schematic view of the instrument for the embodiments presented herein. The instrument 1 for automatically quantifying motility and morphology parameters of the same single motile sperm may include the following components:

(1) a microscope 2, such as an inverted optical microscope. The microscope may also include differential interference contrast (DIC) or phase contrast optics;

(2) a host computer 11 which may include software and processors having instructions for control of the elements of the instrument 1 and for image processing, such as instructions described in FIGS. 2, 3, 8 and 11, including instructions to quantify motility and morphological parameter, instructions to track one or a plurality of motile specimens in a population of motile specimens, instructions to switch from one magnification objective to another magnification objective, instructions to focus an image, instructions to select a motile specimen based on quantified parameters;

(3) a motorized positioner 10, which controls the motion of a sperm container 3. The motorized positioner 10 is operationally connected or linked through wire connection or wireless connection to the host computer 11;

(4) a motorized objective nosepiece 9, which controls the switch of objectives 4, 5 with different magnifications, and is operationally connected or linked or linked through wire connection or wireless connection to the host computer 11;

(5) at least two objective lenses 4, 5, such as a low magnification objective (20× or 40×) and a high magnification objective (60× or 100×), mounted on the motorized objective nosepiece 9; commercial low magnification objective (Nikon Plan Fluor 20×, NA 0.45) with a resolution of 0.61 μm and high magnification objective (Nikon Plan Apo 100×, NA 1.4) with a resolution of 0.20 μm can be used.

(6) an image acquiring unit 8 such as a camera or video camera, which may be mounted on the microscope 2 and be operationally connected or linked through wire connection or wireless connection to the host computer 11; a commercial camera (acA1300-30gc, Basler) can be used.

(7) a focus adjusting motor 6, which may be mounted on the focus adjusting knob and be operationally connected or linked through wire connection or wireless connection to the host computer 11.

The system may also include a vibration isolation table 7 to minimize vibration of the microscope 2, the motorized positioner 10, and the image acquiring unit 8.

The motorized positioner 10, motorized objective nosepiece 9, image acquiring unit 8, focus adjusting motor 6 may be controlled by the host computer 11 so as to automate the measurement of motility and morphology parameters of the same single motile sperm.

Automatically Quantifying Motility and Morphology Parameters of the Same Single Microscopic Motile Specimen In one embodiment the present invention provides for a method of automatically quantifying motility and morphology parameters of a same single microscopic motile specimen.

Motility measurement and morphology measurement have different magnification requirements, but it is infeasible to measure the motility and morphology on the same single sperm in a population of sperm by simply switching the microscope objectives of different magnifications. Because magnification switch changes the microscope field of view (position shift and reduction of the size of field of view when switching from low to high magnification) and because the sperm is fast swimming, the sperm identified in the population of sperm under low magnification will be lost in the field of view after switching to high magnification. The microscope objectives may be mechanically calibrated to align the centers of the field of view between different objective lens, but it can only achieve relocation for a fixed position (i.e., from the center of field of view under low magnification to the center of field of view under high magnification) and cannot relocate the motile sperms appeared at random positions inside the field of view. Furthermore, the inventors found in experiments that sperm movement during magnification switch (which typically takes a few seconds) must also be compensated for in order to prevent it from swimming out of the field of view under high magnification after magnification switch. The speed of the sperm is affected mostly by its physiology and environment. The methods and systems of the present invention can automatically track speeds of up to 300 μm/s, including from 1 μm/s to 300 μm/s. Ranges of speed include up to 250 μm/s, up to 200 μm/s, up to 100 μm/s, up to 75 μm/s, up to 50 μm/s, up to 25 μm/s, up to 15 μm/s, up to 10 μm/s and any ranges therein between.

Figure 2:
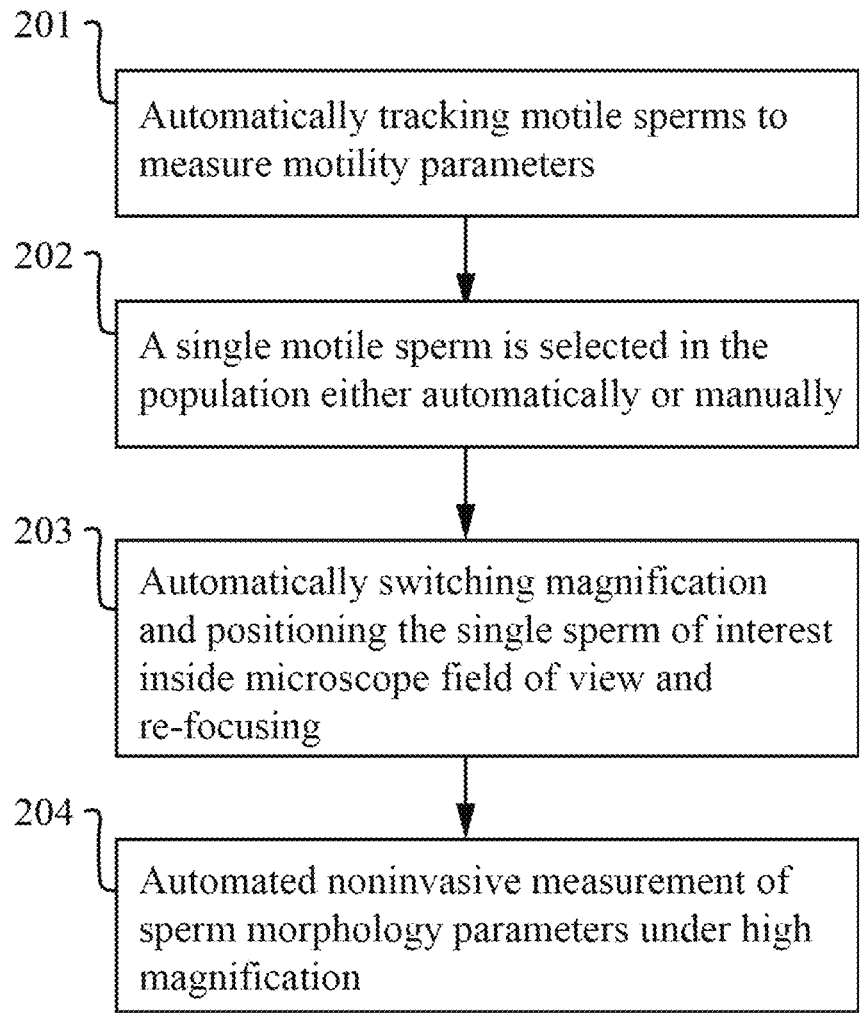
FIG. 2 illustrates an operation sequence of the method for automatically quantifying motility and morphology parameters of the same single motile sperm in accordance to one embodiment of the present invention.

FIG. 2 shows an operation sequence of the method for automatically quantifying motility and morphology parameters of the same single motile sperm in a population of sperm in accordance to one embodiment of the present invention. The sequence starts by automatically tracking multiple motile sperms in the population of sperm under low magnification to determine motility parameters (Step 201).

Sperm crossing over and swimming in close proximity are prevalent in clinical samples and can cause mismatch of tracked sperms, requiring robust tracking methods to accurately quantify each sperm's motility parameters. The inventors have tested a variety of methods commonly used for multiple object tracking and quantitatively evaluate their performance on sperm tracking. The tested methods include nearest neighbor, global nearest neighbor, direction vector, multiple hypothesis tracker, and joint probabilistic data association filter (JPDAF). The nearest neighbor method is the most widely used method in computer assisted sperm analysis (CASA), and is implemented by associating the nearest sperm in the present image frame to the tracked sperm in the last image frame as the same one. Inventors' previous publications (C. Leung, Z. Lu, N. Esfandiari, R. F. Casper, and Y. Sun, "Automated sperm immobilization for intracytoplasmic sperm injection," IEEE Trans. Biomedical Engineering, Vol. 58, pp. 935-942, 2011; Z. Lu, X. P. Zhang, C. Leung, N. Esfandiari, R. F. Casper, and Y. Sun, "Robotic ICSI (Intracytoplasmic Sperm Injection)," IEEE Trans. Biomedical Engineering, Vol. 58, pp. 2102-2108, 2011; J. Liu, C. Leung, Z. Lu, and Y. Sun, "Quantitative analysis of locomotive behavior of human sperm head and tail," IEEE Trans. Biomedical Engineering, Vol. 60, pp. 390-396, 2013) used methods of nearest neighbor and direction vector (time-averaged swimming direction of sperms) to distinguish sperms under interference. Experimental results show JPDAF is superior to other methods in multiple sperm tracking and has the highest tracking accuracy of 81.2%. JPDAF works by enumerating all association cases between targets and measurements and updating association probability and better handles intersection and close proximity of sperms. Nevertheless, aforementioned methods only employ kinematic parameters such as the position and velocity for sperm tracking, and kinematics alone is not sufficient for robust tracking especially when two sperms intersect.

The JPDAF was adapted in this invention by incorporating the head orientation of the sperm. Head orientation is defined as the angle between the major axis of the sperm head and the horizontal axis of the image. Experimental results show that the adapted JPDAF achieved a higher tracking accuracy of 95.6% (vs. 81.2% by standard JPDAF). It should be understood that the aforementioned head orientation is only one example for identifying each sperm in close proximity and intersection. Other morphology information, such as the head shape, may also be incorporated for achieving more robust sperm tracking.

Based on tracked sperm trajectories, motility parameters are quantified, including VCL (curvilinear velocity), VSL (straight-line velocity), VAP (average path velocity), ALH (amplitude of lateral head displacement), LIN (linearity), WOB (wobble), STR (straightness), BCF (beat-across frequency), and MAD (mean angular displacement).

Table 1 illustrates the maximum speed that can be tracked with the methods of the present invention per objective magnification. This upper speed limit is determined by the microscope's field of view and the tracking algorithm of the present invention.

TABLE 1

| Objective magnification (X) | Maximum trackable speed (µm/s) |
|---|---|
| 0.5 | 48000 |
| 1.25 | 19200 |
| 1.5 | 16000 |
| 2 | 12000 |
| 2.5 | 9600 |
| 5 | 4800 |
| 10 | 2400 |
| 20 | 1200 |
| 40 | 600 |
| 50 | 480 |
| 100 | 240 |
| 150 | 160 |

Figure 3:
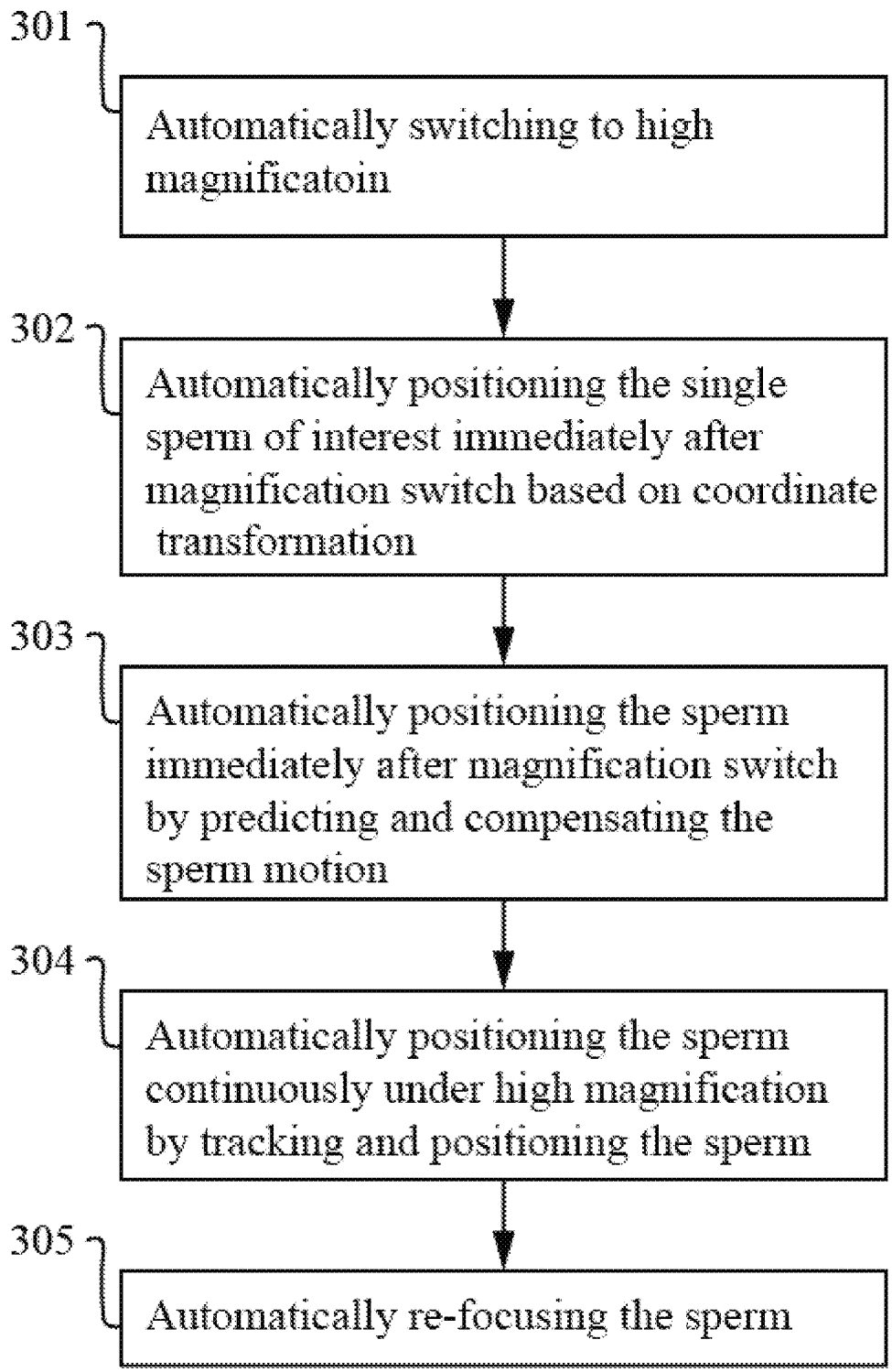
FIG. 3 illustrates an operation sequence of automatically switching to high magnification and automatically positioning the same single motile sperm, which has been imaged and measured under low magnification, and re-focusing on the sperm.

After motility measurement, in step 202 a single motile sperm is selected in the population either automatically by the computer program (see Section C) or by an operator (e.g., via computer mouse clicking) for morphology measurement under high magnification. Because switching microscope magnification changes the field of view of a microscope and the sperm is moving during magnification switch, the same motile sperm must be relocated inside microscope field of view after magnification switch. In Step 203, the method involves automatically switching to high magnification and automatically positioning the selected single motile sperm of interest (selected under low magnification) inside microscope field of view and re-focusing on the selected sperm. The operation sequence of automatically switching to high magnification and automatically positioning the selected single motile sperm and re-focusing on the selected sperm is shown in FIG. 3. Automatically switching to high magnification (Step 301) is achieved by a motorized objective nosepiece controlled by the host computer. Automatically positioning the selected single motile sperm inside microscope field of view comprises positioning immediately after magnification switch (Step 302, 303) and positioning continuously under high magnification (Step 304).

After magnification switch, the same sperm is immediately positioned in the microscope field of view by the calibrated coordinate transformation (Step 302) and by predicting and compensating for the motion of the motile sperm during magnification switch (Step 303). Besides calibrated coordinate transformation, an alternative approach is to mechanically align the centers of the field of view between different microscope objectives. However, this approach can only achieve relocation for a fixed position (i.e., from the center of field of view under low magnification to the center of field of view under high magnification) and cannot relocate motile sperms present in random positions inside field of view. Additionally, the alignment of objectives still cannot compensate for the movement of the target sperm during magnification switch, which will cause the sperm swimming out of the field of view after switching to high magnification.

Figure 4:
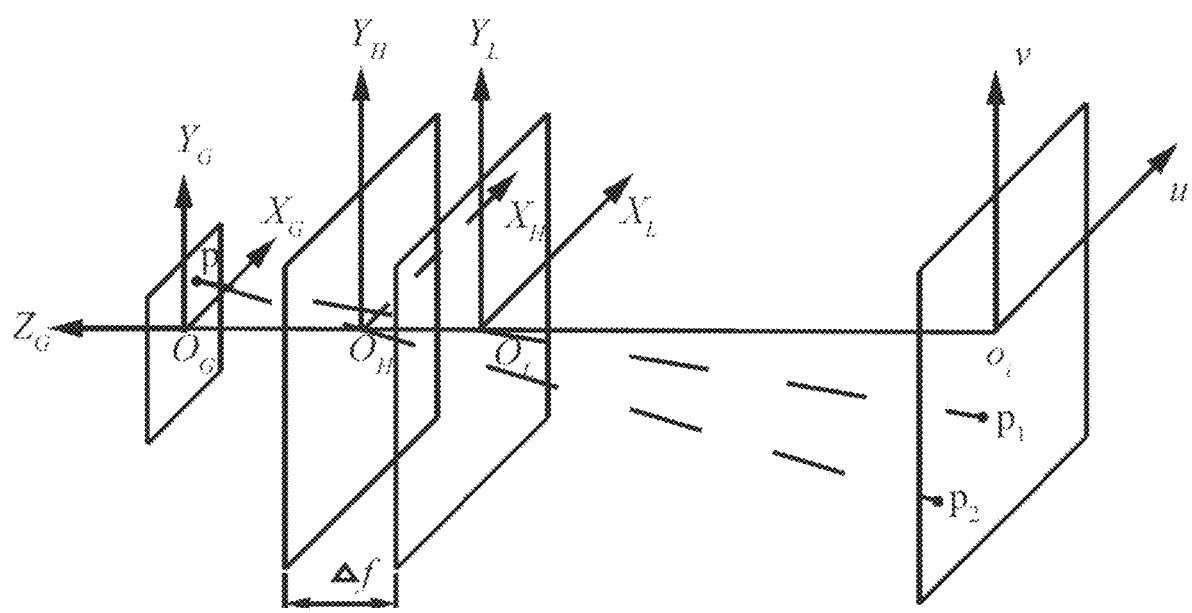
FIG. 4 illustrates the coordinate transformation for a microscope with objectives of different magnifications.

Coordinate transformation establishes the relationship of image coordinates under microscope objectives of different magnifications. FIG. 4 shows the global coordinate system ($O_G$-$X_G Y_G Z_G$), low magnification objective plane ($O_L$-$X_L Y_L$), high magnification objective plane ($O_H$-$X_H Y_H$), and the image plane ($o_i$-uv).

Transformation in the image plane from the coordinate vector $U_L$ under low magnification to the coordinate vector $U_H$ under high magnification is $$U_H = \begin{bmatrix} u_h \\ v_h \\ 1 \end{bmatrix} = KU_1 = \begin{bmatrix} k_u & 0 & t_u \\ 0 & k_v & t_v \\ 0 & 0 & 1 \end{bmatrix} \begin{bmatrix} u_l \\ v_l \\ 1 \end{bmatrix} \quad (1)$$

where K is the transformation matrix from low magnification to high magnification, $k_u$ and $k_v$ are magnification factors along the u and v axis, respectively. $t_u$ and $t_v$ are translation factors along the u and v axis.

The transformation from the coordinate vector $U_H$ under high magnification to the coordinate vector $U_L$ under low magnification is $$U_L = K^{-1} U_H \quad (2)$$

The transformation matrix K is obtained using the least square method.

$$K = \tilde{U}_H \tilde{U}_L^T (\tilde{U}_L \tilde{U}_L^T)^{-1} \quad (3)$$

where $\tilde{U}_L$ and $\tilde{U}_H$ are 3×N matrixes storing N coordinate vectors under low magnification and high magnification, respectively.

This coordinate transformation is used to compensate for the translation of image coordinates under objectives of different magnifications. During magnification switch, the image coordinates of a sperm under a low magnification objective are transformed to the corresponding image coordinates under a high magnification objective. Then the motorized positioner controls the position of the selected single sperm to the desired image coordinates (e.g. the center of field of view) under a high magnification objective. The coordinate transformation may be calibrated using a grid calibration slide.

The immediate sperm positioning after magnification switch also includes predicting and compensating for the motion of the motile sperm during the switch (Step 303). The prediction of sperm positions during magnification switch is based on the computer vision-tracked head and tail positions of the sperm before the switch. The tail of the sperm may be tracked using methods such as motion history image and Kalman filter. Let Δt denote the time needed for switching from the low-magnification objective to the high-magnification objective. The sperm's position P after magnification switch is predicted as $$P = \begin{bmatrix} x \\ y \end{bmatrix} = \begin{bmatrix} x_{prev} \\ y_{prev} \end{bmatrix} + \Delta t \cdot v \cdot \begin{bmatrix} \cos\theta \\ \sin\theta \end{bmatrix} \quad (4)$$

where (x, y) is the predicted position of the sperm head or tail after magnification switch, and ($x_{prev}$, $y_{prev}$) is the measured position of the sperm head or tail before magnification switch, v and θ are the swimming velocity and head orientation of the sperm, respectively.

The same sperm is continuously positioned in the microscope field of view under high magnification by visual tracking and automated positioning the sperm at the center of field of view to compensate for the sperm motion (Step 304). Sperm tracking may be implemented using methods such as joint probabilistic data association filter.

The switch of microscope objectives also changes microscope focus. Automatically re-focusing of the sperm (Step 305) is achieved by driving the motor mounted on the focus adjusting knob of the microscope to compensate for calibrated change of focal length (Δf in FIG. 4). Focus may also be automatically adjusted according to the calculation of focus measures of images. The focus measure of the image may be evaluated using metrics such as normalized variance and entropy.

Although the method of automatically switching to high magnification and automatically positioning the single motile sperm inside microscope field of view and re-focusing on the sperm presented herein above may relate to automatically positioning and re-focusing of sperm after magnification switch, it should be expressly understood that this is an illustrative example only and that the present invention is readily adaptable for automatically positioning and re-focusing of any other motile specimen having or not having a tail portion after magnification switch.

Finally, referring back to FIG. 2 (Step 204), the method achieves automated non-invasive measurement of sperm subcellular morphology under high magnification, which is described in detail in the next section. It should be expressly understood that the operation sequence as shown in FIG. 2 may repeat several times for the motility and morphology measurement of multiple single sperms for analysis, comparison, and selection.

Figure 5:
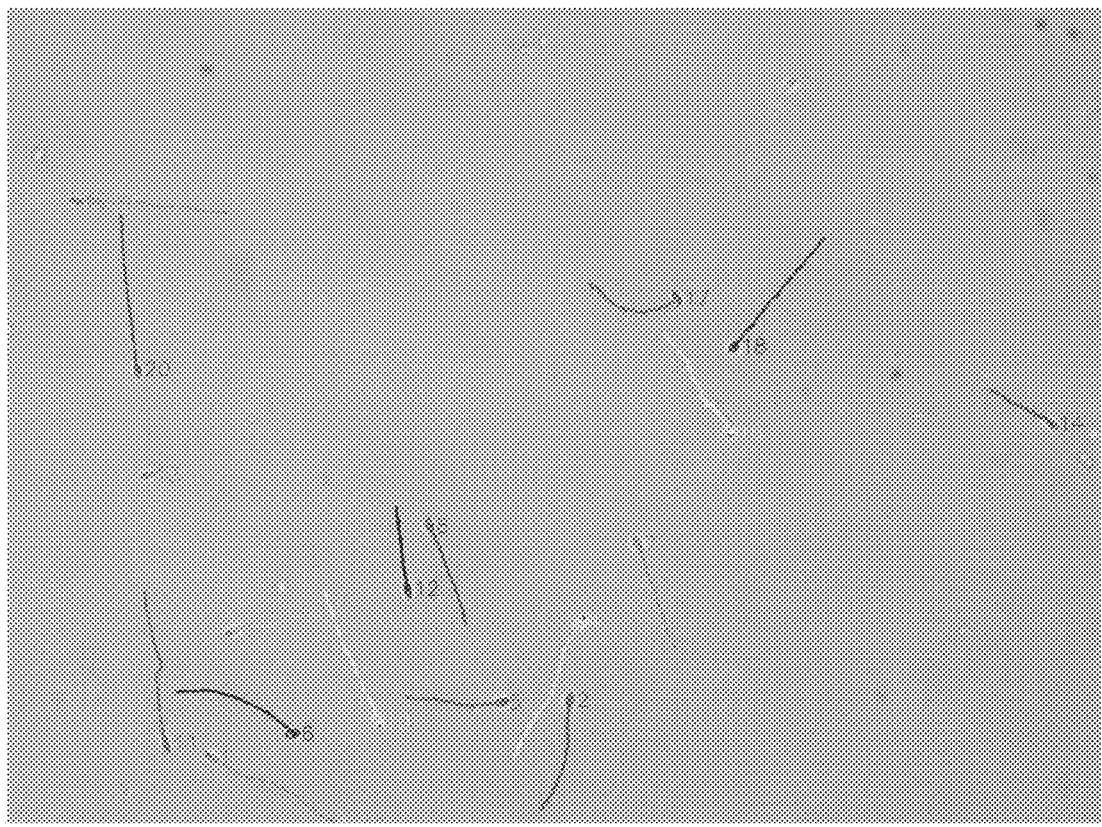
FIG. 5 shows a sample image illustrating sperm identification and tracking under low magnification for motility measurement.
Figure 6A:
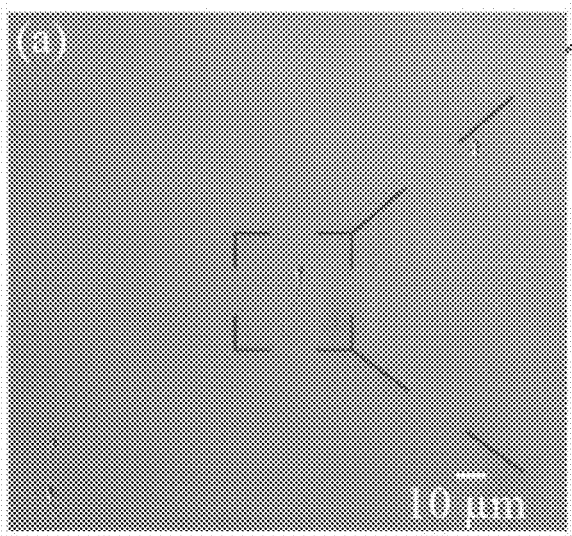
FIGS. 6A and 6B show a sample image illustrating automatically switching from a low magnification (FIG. 6A) to high magnification (FIG. 6B) and automatically positioning the single motile sperm of interest inside microscope field of view and re-focusing on the sperm.
Figure 6B:
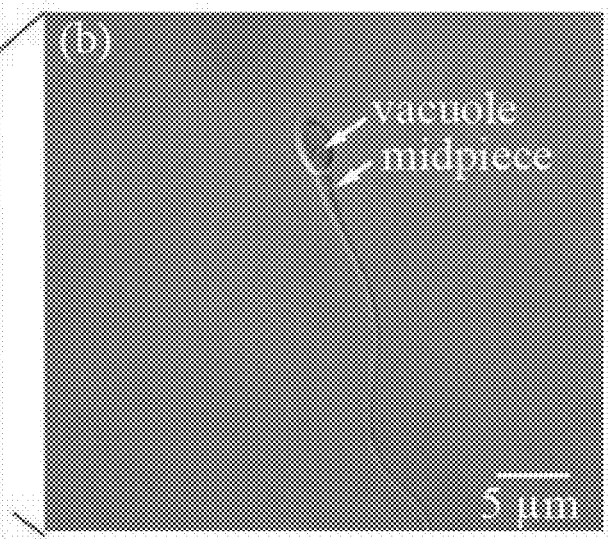

FIG. 5 shows a sample image illustrating sperm identification and tracking under low magnification for motility measurement. Only the trajectories of motile sperms are marked on the image. FIGS. 6A and 6B show a sample image illustrating automatically switching from a low magnification (FIG. 6A) to high magnification and automatically positioning the single motile sperm of interest inside microscope field of view and re-focusing on the same sperm (FIG. 6B).

Automated Non-Invasive Measurement of Morphology Under High Magnification

In another embodiment the present invention provides for a method of automated non-invasive measurement of morphology of a microscopic motile specimen under relative high magnification. High magnification such as 100× objective is used for visualizing and measuring sperm subcellular structures (e.g., acrosome and vacuoles). Brightfield images under high magnification may not have sufficient contrast to visualize sperm subcellular structures. Differential interference contrast (DIC) or phase contrast imaging non-invasively increases image contrast by visualizing the difference in optical path length or phase and may be used to increase the contrast of the microscopic specimen image under high magnification.

Presently, embryologists qualitatively observe sperm morphology, which involves inherent subjectivity and inconsistency. Additionally, the visualization of subcellular structures such as vacuoles on the sperm head requires a high magnification; however, the low contrast of live sperms under high magnification (even in the DIC or phase contrast imaging mode) makes the observation difficult. To increase the contrast, the sperms are fixed and stained but it makes the sperms after measurement not usable for infertility treatment. The present invention provides a method of automated measurement of sperm morphology without invasive staining, and the sperm after measurement can be selected for infertility treatment.

Figure 7:
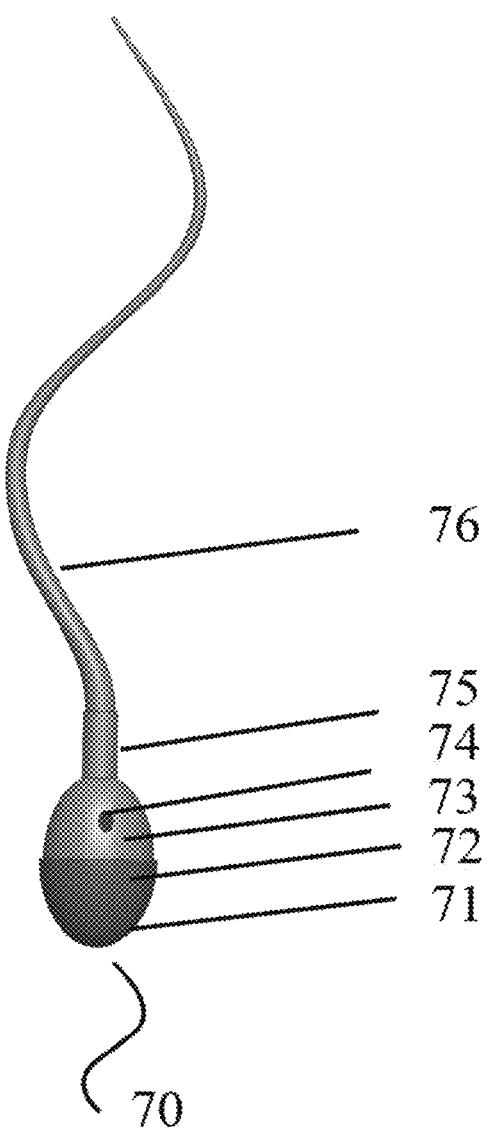
FIG. 7 illustrates a schematic view of the sperm and its subcellular structures under high magnification.

A schematic view of the sperm and its subcellular structures under high magnification is shown in FIG. 7. A sperm 70 may be divided into three parts: head 71, midpiece 75, and tail 76. The head 71 may be divided into acrosome 72 and nucleus 73. The acrosome 72 covers the anterior part of the head 71. Vacuole 74 may exist on the sperm head 71.

Figure 8:
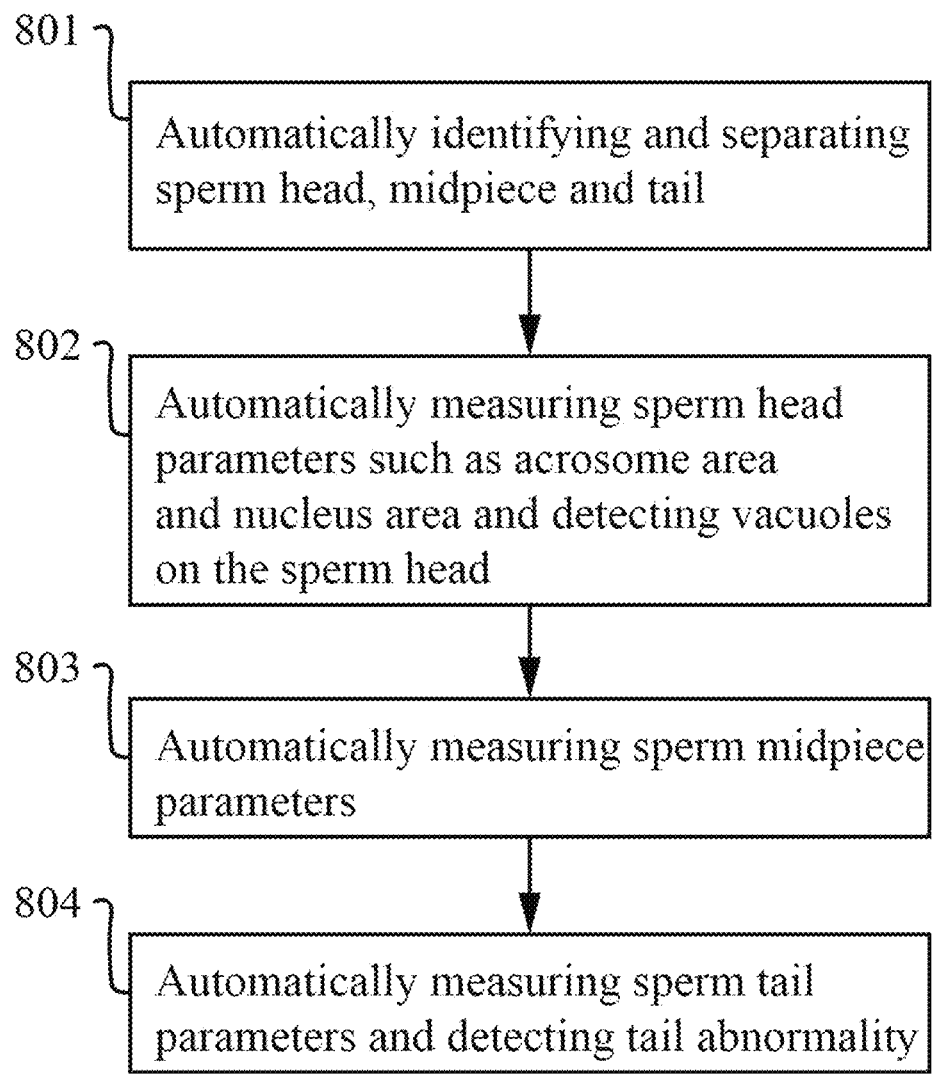
FIG. 8 illustrates an operation sequence of automated non-invasive measurement of sperm morphology under high magnification in accordance to one embodiment of the present invention.

The measured morphology parameters include head size and shape, acrosome area, nucleus area, vacuole number, vacuole area, midpiece size, midpiece angle, excess residual cytoplasm, tail length, and tail abnormality. The operation sequence of automated non-invasive measurement of sperm morphology under high magnification is shown in FIG. 8. The sequence starts by identifying and separating different parts of a sperm: head, midpiece and tail (Step 801). To separate the different parts of the sperm, we first tried the method of image morphological erosion and dilation to retain the sperm head while removing the tail. But this method significantly changes the original shape of the sperm head and reduces the accuracy of morphology measurement. We also tested segmentation of the sperm head and tail by their shape difference (an ellipse and a line, respectively), but it was difficult to separate the midpiece and tail due to their similar shape. We eventually achieved satisfactory separation results by measuring the width differences of the head, midpiece and tail. The width may be measured by quantifying the distance from points on the contour of the sperm to the centerline of the sperm. The centerline of the sperm may be obtained from iterative thinning of the binarized image of the sperm.

For the sperm head, acrosome and nucleus areas are automatically measured under high magnification by detecting regions on the sperm head having different pixel intensities (Step 802). Contrast difference of the acrosome and nucleus may be caused by inherent difference of refractive index and be visualized by DIC or phase contrast imaging. Detecting regions with different contrast may be achieved by methods such as watershed and region growing. FIG. 9 shows a sample image illustrating the separation of sperm head, midpiece and tail, and the detection of nucleus region under high magnification of 100×. The boundaries of different parts are marked on the image of FIG. 9B. Vacuoles on the sperm head are detected by detecting the holes on the sperm head in binarized high magnification images. Detecting the holes may be achieved by methods such as Hough transform and template matching. FIG. 10 shows a sample image illustrating the detection of a vacuole on the sperm head under high magnification. The boundaries of different parts are marked on the image of FIG. 10B. In step 803, sperm midpiece parameters including midpiece size and angle are automatically measured by methods such as minimum bounding box and convex hull. Excess residual cytoplasm on the midpiece may be detected by inspecting abnormal width of the midpiece.

It should be understood that the aforementioned algorithm of detecting regions with different pixel intensities is only one example for detecting acrosome and nucleus regions. Other visual information, such as the interface between the acrosome and the nucleus may also be used to detect acrosome and nucleus regions.

For the sperm tail, tail abnormality is automatically detected (Step 804). Tail abnormality includes coiling, bending, and width non-uniformity. Tail coiling is automatically detected by detecting closed contours on the sperm tail. Tail bending is automatically detected by detecting the sharp turn of the centerline of the sperm tail. Tail width non-uniformity is automatically detected by measuring the distribution of the distance from points along the tail contour to the centerline of the sperm tail.

The method of automated non-invasive measurement of sperm morphology may be performed either on motile sperm positioned continuously inside the microscope field of view, or on immobilized sperm. Sperm immobilization may be implemented by touching the sperm tail with a micropipette. Immobilization may help visualize sperm subcellular structures more clearly by preventing the rotational motion of the motile sperm head.

Quantitative Automated Selection of Single Specimen with Normal Motility and Morphology In another embodiment the present invention provides for a method for quantitative automated selection of sperms with normal motility and morphology for infertility treatment. The selection is based on the quantitative measurement of an individual (i.e. the same) sperms' motility and morphology under different magnifications. In this document, as it will be explained below, "normal motility" of a sperm refers to a sperm having curvilinear velocity (VCL) of about 25 µm/s or higher, and linearity (LIN) higher than 0.9, or to a sperm having straight-line velocity (VSL) greater than 20 µm/s. In this document "normal morphology" in a sperm refers to a sperm with head length-width ratio between about 1.5 to about 1.75, and without head abnormality such as vacuole. Other parameters that may be used to determine a sperm with "normal morphology" include a sperm without midpiece abnormality, and/or without tail abnormality. The sperm vacuole is a concavity extending from the surface of the sperm head to the nucleus, indicating fragmented or damaged sperm DNA. Midpiece abnormalities include abnormal midpiece size and angle, and excess residual cytoplasm (i.e., existence of cytoplasmic droplet). Tail abnormality includes coiling, bending, and width non-uniformity. It should be understood that this method may also be applied to other motile microscopic specimens for selection of specific motility and morphological parameters.

Sperm selection for infertility treatment currently relies on embryologists' experience by qualitatively observing sperms' motility and morphology, and manual quantitative estimation may be assisted by the ocular micrometer fixed on the microscope eyepiece. As manual selection is qualitative and the definition of a normal sperm varies among embryologists, the method provided by the present invention enables quantitative selection of sperms with normal motility and morphology. The criteria for quantitative sperm selection are based on the experiments the inventors have conducted on determining the range of motility and morphology parameters that indicate sperms with high DNA integrity (i.e., without DNA fragmentation). DNA fragmentation of sperms may cause fertilization failure, embryo development arrest or miscarriages. Existing criteria such as the WHO criteria and the Strict criteria were established by examining a population of sperms recovered from the female reproductive tract especially from endocervical mucus and the surface of the zona pellucida, as it is assumed that the sperms reaching these sites have higher fertilization potential. But using these criteria does not enable the selection of a single sperm with high DNA integrity. In our experiments, after measuring individual sperms' motility and morphology parameters using the automated methods disclosed in this invention, we performed Comet assay (single cell electrophoresis) on each sperm to measure its DNA fragmentation. The criteria of normal motility and morphology were obtained from those single sperms that had high DNA integrity; thus, the criteria we provide can determine normal motility and morphology indicating high DNA integrity of the sperm. These criteria are exclusively enabled by our techniques, due to the capability of quantitatively measuring the same sperm's motility and morphology parameters and directly correlating these parameters with the same sperm's DNA integrity. Using the quantitative criteria, sperms with normal motility and normal morphology and potentially with high DNA integrity can be automatically selected for infertility treatment.

Figure 11:
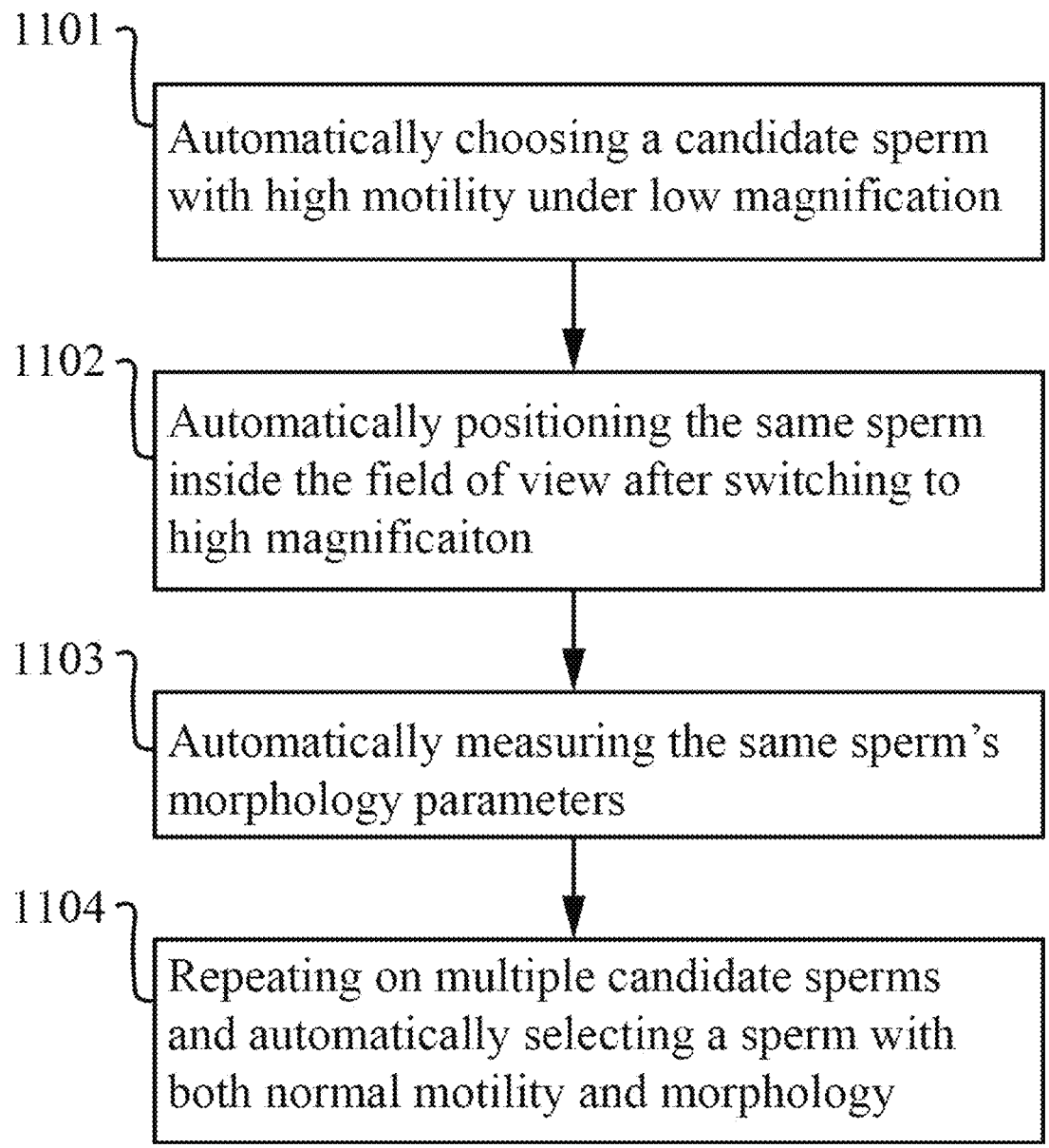
FIG. 11 illustrates an operation sequence of quantitative automated selection of sperm with normal motility and morphology in accordance to another embodiment of the present invention.

The operation sequence of automated selection of single sperm with normal motility and morphology is shown in FIG. 11. The sequence starts by automatically choosing a candidate sperm with normal motility after motility measurement under low magnification (or first magnification) (Step 1101). The motility measurement is achieved by tracking multiple motile sperms as discussed before. A motile sperm with the normal motility inside the field of view is automatically chosen for further morphology measurement. The same sperm is automatically positioned inside the field of view after switching to high magnification (or second magnification) (Step 1102). In Step 1103, the sperm's morphology parameters are automatically measured. The aforementioned steps are repeated on multiple candidate sperms and a sperm with both normal motility and morphology is automatically selected (Step 1104).

One skilled in the art understands that when a sperm is selected under low magnification, it is difficult, if not impossible, to identify the selected sperm when switching to high magnification.

By quantitatively measuring DNA fragmentation of a single sperm and by correlating it with the same sperm's motility and morphology parameters, we experimentally established a preferred criteria of selecting sperms with high DNA integrity:

straight-line velocity (VSL) equal or greater than 20 µm/s or curvilinear velocity (VCL) equal or greater than 25 µm/s with linearity (LIN) equal or higher than 0.9; and Head having a length-width ratio between 1.5 to 1.75 and without vacuole.

Selection of sperms with high DNA integrity can be achieved with the motility criteria and the sperm's head morphology criteria alone. Other morphological criteria that can be used in addition to the head's morphology include a sperm:

without midpiece abnormality; and/or without tail abnormality.

That is, sperms with high DNA integrity can be selected on the basis of sperms having both a normal motility and a normal morphology, wherein the normal morphology can be determined on the basis of the head morphology alone, or the combination of the head and mid-piece morphologies, or the combination of the head and tail morphologies, or the combination of the head, mid-piece and tail morphologies.

Figure 12:
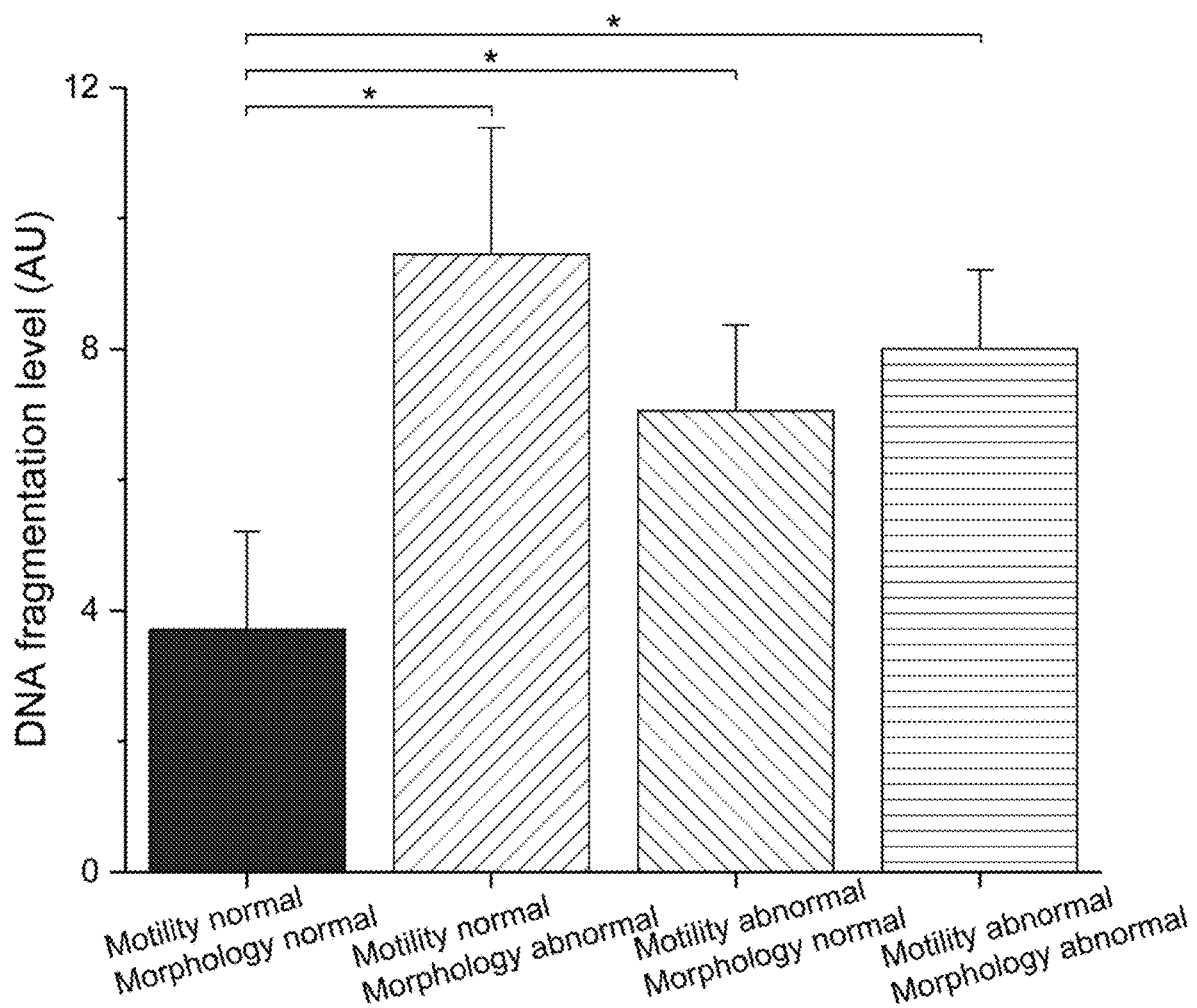
FIG. 12 shows sperm that were selected by using the quantitative criteria of both motility (VSL equal or greater than 20 μm/s) and morphology (sperm's head having a length-width ratio between 1.5-1.75, mid-piece without abnormalities and tail without abnormalities) had significantly lower DNA fragmentation (i.e., higher DNA integrity) than those only meeting motility or morphology criteria and those not meeting either criteria. Each group had 50 sperm, 200 sperm in total.

These parameters are all computer-measured according to methods in Section A and B (see Step 201, 802, and 804). The quantitative criteria of both motility and morphology must be met at the same time, for selecting a sperm with high probability of DNA integrity. The criteria were experimentally validated by comparing the DNA fragmentation of the selected sperms using the criteria and the sperms not meeting the criteria. The experimental results in FIG. 12 show the sperms selected by using the quantitative criteria of both motility (VSL equal or greater than 20 μm/s) and morphology (head length-width ratio between about 1.5 to about 1.75, without vacuole, without midpiece abnormality, and without tail abnormality) had significantly lower DNA fragmentation (i.e., higher DNA integrity) than those only meeting motility or morphology criteria and those not meeting either criteria. DNA fragmentation level of a single sperm was measured by conducting the Comet assay (single cell gel electrophoresis).

According to an embodiment, the quantitative criteria of both motility and morphology must be met at the same time, for selecting a sperm with high probability of DNA integrity. Under one embodiment, the sperm has a head length-with ratio of about 1.5 to 1.75, no vacuole and a velocity VSL for which the DNA integrity is suitable for sperm selection, e.g, VSL≥0 μm/s, VSL≥5 μm/s, VSL≥10 μm/s, VSL≥15 μm/s or preferably VSL≥20 μm/s or VSL≥25 μm/s. According to another embodiment, the sperm has a head length-with ratio of about 1.5 to 1.75, no vacuole, no midpiece abnormality and a velocity VSL for which the DNA integrity is suitable for sperm selection, e.g., VSL≥0 μm/s, VSL≥5 μm/s, VSL≥10 μm/s, VSL≥15 μm/s or preferably VSL≥20 μm/s or VSL≥25 μm/s. According to another embodiment, the sperm has a head length-with ratio of about 1.5 to 1.75, no vacuole, no tail abnormality and a velocity VSL for which the DNA integrity is suitable for sperm selection, e.g., VSL≥0 μm/s, VSL≥5 μm/s, VSL≥10 μm/s, VSL≥15 μm/s or preferably VSL≥20 μm/s or VSL≥25 μm/s. According to another embodiment, the sperm has preferably a head length-with ratio of about 1.5 to 1.75, no vacuole, no midpiece abnormality, no tail abnormality and a velocity VSL for which the DNA integrity is suitable for sperm selection, e.g, VSL≥0 μm/s, VSL≥5 μm/s, VSL≥10 μm/s, VSL≥15 μm/s or preferably VSL≥20 μm/s or VSL≥25 μm/s.

According to another embodiment, the quantitative criteria of both motility and morphology must be met at the same time, for selecting a sperm with high probability of DNA integrity. Under one embodiment, the sperm has a head length-with ratio of about 1.5 to 1.75, no vacuole and a velocity VCL for which the DNA integrity is suitable for sperm selection, e.g, VCL≥0 μm/s, VCL≥5 μm/s, VCL≥10 μm/s, VCL≥15 μm/s or preferably VCL≥20 μm/s or VCL≥25 μm/s with a LIN higher than 0.9. According to another embodiment, the sperm has a head length-with ratio of about 1.5 to 1.75, no vacuole, no mid-piece abnormality and a velocity VCL for which the DNA integrity is suitable for sperm selection, e.g, VCL≥0 μm/s, VCL≥5 μm/s, VCL≥10 μm/s, VCL≥15 μm/s or preferably VCL≥20 μm/s or VCL≥25 μm/s with a LIN higher than 0.9. According to another embodiment, the sperm has a head length-width ratio of about 1.5 to 1.75, no vacuole, no tail abnormality and a velocity VCL for which the DNA integrity is suitable for sperm selection, e.g, VCL≥0 μm/s, VCL≥5 μm/s, VCL≥10 μm/s, VCL≥15 μm/s or preferably VCL≥20 μm/s or VCL≥25 μm/s with a LIN higher than 0.9. According to another embodiment, the sperm has preferably a head length-with ratio of about 1.5 to 1.75, no vacuole, no mid-piece abnormality, no tail abnormality and a velocity VCL for which the DNA integrity is suitable for sperm selection, e.g., VCL≥0 μm/s, VCL≥5 μm/s, VCL≥10 μm/s, VCL≥15 μm/s or preferably VCL≥20 μm/s or VCL≥25 μm/s with a LIN higher than 0.9.

Table 2 summarize the results measured on 300 human sperms. It shows the percentage of sperms satisfying all the morphology criteria ["normal morphology" refers to head length-width ratio between about 1.5 to about 1.75, without vacuole, without midpiece abnormality, and without tail abnormality] with varying straight-line velocity (VSL). For each VSL threshold, the probability of DNA integrity of those sperms was quantified. For instance, when VSL is equal to and above 20 μm/sec, the probability that the sperm had high DNA integrity was 94.1%, and the percentage of sperms satisfying this VSL threshold was 5.6% of the 300 measured sperms. When the VSL threshold was 25 μm/sec, although the probability of high DNA integrity increased to 100%, the percentage of sperms satisfying the VSL threshold became too low (0.7%). Thus, for practicality, VSL threshold was set to be 20 μm/sec for sperm selection.

TABLE 2

| VSL threshold (μm/s) | Percentage of sperm satisfying criteria | Probability of high DNA integrity |
| --- | --- | --- |
| 0 | 32.1% | 74.2% |
| 5 | 31.5% | 75.8% |
| 10 | 28.8% | 77.0% |
| 15 | 16.6% | 78.0% |
| 20 | 5.6% | 94.1% |
| 25 | 0.7% | 100.0% |

The sperms automatically selected with normal motility and morphology may be recommended to the operator/embryologist who can confirm whether to use the sperm for IVF treatment. If the operator disagrees with the selection, the automated selection will iterate until finding a normal sperm which the operator agrees to use.

Aspects described herein can be embodied in other forms and combinations without departing from the spirit or essential attributes thereof. Thus, it will of course be understood that embodiments are not limited to the specific details described herein, which are given by way of example only, and that various modifications and alterations are possible.

What is claimed is:

1. A computer implemented method of automatically quantifying motility and morphology parameters of a single motile microscopic specimen in a population of motile specimens using a computer, characterized in that said method comprises the following steps:
(a) placing, or enabling the placement of, the population of motile microscopic specimens on a stage of a microscope means, the microscope means having (i) a motorized positioner controlling the motion of the stage, (ii) a motorized objective nosepiece, (iii) a first microscope magnification objective and a second magnification objective mounted on the motorized objective nosepiece, the second magnification objective having a higher magnification power than the first magnification objective, (iv) an image acquiring unit mounted on the microscope means, and (v) a focus adjusting motor, the motorized positioner, motorized objective nosepiece, the image acquiring unit and the focus adjusting motor being operationally connected to the computer;

(b) automatically obtaining images of the population of motile microscopic specimens using the image acquiring unit through the first microscope magnification objective;

(c) automatically moving the motorized positioner for tracking a plurality of motile microscopic specimens in the population based on the images taken through the first microscope magnification objective to quantify the motility parameters of the tracked motile microscopic specimens;

(d) selecting a single motile microscopic specimen using the quantified motility parameters;

(e) automatically (i) switching to a second magnification objective using the motorized nosepiece, (ii) positioning said selected single motile microscopic specimen inside a field of view of said second magnification objective using the motorized positioner, (iii) re-focusing on the single motile microscopic specimen using the focus adjusting motor, and (iv) obtaining images with the image acquiring unit of the single motile microscopic specimen through the second magnification objective; and (f) quantitatively measuring morphology parameters of said selected single motile microscopic specimen using the microscopic images taken with the second magnification objective.

2. The method of claim 1, wherein
(i) said automatically positioning is based on a calibrated coordinate transformation and prediction of the selected single motile microscopic specimen position, wherein said calibrated coordinate transformation compensates for a change of field of view and focus after the first magnification objective is switched to the second magnification objective; or
(ii) said motility measurement includes VCL (curvilinear velocity), VSL (straight-line velocity), VAP (average path velocity), ALH (amplitude of lateral head displacement), LIN (linearity), WOB (wobble), STR (straightness), BCF (beat-across frequency), MAD (mean angular displacement), or a combination thereto; or
(iii) both of the above.

3. The method of claim 2, wherein
(i) said prediction of the single motile microscopic specimen position compensates for the motion of the single motile specimen during magnification switch; or
(ii) said motile microscopic specimen is sperm, and wherein said prediction of the single sperm position is based on a sperm head position or a sperm tail position measured under the first magnification; or
(iii) said positioning of said motile specimen is performed continuously under the second magnification objective by tracking and positioning said motile sperm to compensate for the sperm motion after magnification switch.

4. The method of claim 1, wherein said visual tracking is achieved by a joint probabilistic data association filter (JPDAF).

5. The method of claim 4, wherein said motile microscopic specimen is a sperm and wherein the joint probabilistic data association filter (JPDAF) is adapted by incorporating a sperm head orientation and morphology features of the sperms to differentiate the tracked individual sperms during crossing over and close proximity of sperms in a population of sperm.

6. The method of claim 5, wherein
(i) said head orientation is defined as an angle between the major axis of the sperm head and the horizontal axis of the image; or
(ii) said morphology features include a head shape of the sperm; or
(iii) both of the above.

7. The method of claim 1, wherein the method further comprises repeating steps (a) to (c) for other motile microscopic specimens in the population, and wherein the method further comprises selecting a candidate motile microscopic specimen based on a quantitative comparison amongst the selected motile microscopic specimens in measured motility and measured morphological parameters.

8. The method of claim 7, wherein said selection of the candidate motile microscopic specimen is achieved by finding motile microscopic specimen with measured motility and morphology parameters meeting a predetermined quantitative criteria of motility and morphology.

9. The method of claim 8, wherein
(i) said predetermined quantitative criteria of motility and morphology are determined by finding a range of motility and morphological parameters which indicate high DNA integrity of the motile microscopic specimen; or
(ii) said predetermined quantitative criteria of both motility and morphology must be met at the same time, for selecting a sperm with high probability of DNA integrity; or
(iii) both of the above.

10. The method of claim 8, wherein the motile microscopic specimen is sperm, and wherein said predetermined quantitative criteria of motility include a curvilinear velocity (VCL) equal or greater than 20 μm/s, linearity (LIN) higher than 0.9, and said predetermined quantitative criteria of morphology include a sperm head length-width ratio between 1.5 to 1.75, without vacuole.

11. The method of claim 10, wherein said predetermined quantitative criteria of morphology further include a sperm without midpiece abnormality, or a sperm without tail abnormality and without midpiece abnormality, or a sperm without tail abnormality.

12. The method of claim 8, wherein the motile microscopic specimen is sperm, and wherein said quantitative criteria of motility and morphology are a straight-line velocity (VSL) equal or greater than 10 μm/s, and said predetermined criterial of morphology include a sperm's head having a length-width ratio between 1.5 to 1.75, without vacuole.

13. The method of claim 12, wherein
(i) the VSL is equal or greater than 20 μm/s; or
(ii) said predetermined quantitative criteria of morphology further include a sperm without midpiece abnormality, or a sperm without tail abnormality and without midpiece abnormality, or a sperm without tail abnormality; or
(iii) both of the above.

14. A method for automated non-invasive measurement of a morphological feature or features of a live, unstained motile microscopic specimen, comprising:
(a) automatically segmenting the morphological feature or features of the motile microscopic specimen under a microscope, and
(b) automatically measuring the morphological feature or features under the microscope wherein (i) step (a) comprises automatically segmenting at least two morphological features of the motile microscopic specimen;

(ii) the morphological feature is the sperm's midpiece, and abnormalities in midpiece size and midpiece angle are measured by a minimum bounding box or a convex hull;

(iii) the morphological feature is the sperm's midpiece, and an excess residual cytoplasm on the midpiece is detected by inspecting abnormal width of the midpiece; or (iv) the morphological feature is the tail, and (a) an abnormality in tail coiling is automatically detected by detecting closed contours on the sperm tail; (b) an abnormality in tail bending is automatically detected by detecting a sharp turn in a centerline of the sperm tail; and (c) an abnormality of tail width non-uniformity is automatically detected by measuring a distribution of a distance from points along the tail's contour to a centerline of the sperm tail; or (v) any combination of the above.

15. The method of claim 14, wherein the motile specimen is sperm, and wherein said sperm morphological feature or features include one or more of the sperm's head, midpiece and tail, and wherein the sperm morphological feature or features are separated in an image by measuring width differences of the head, the midpiece and the tail.

16. The method of claim 15, wherein said width is measured by quantifying a distance from points on a contour of the sperm to a centerline of the sperm.

17. The method of claim 16, wherein said centerline is obtained by iterative image thinning.

18. The method of claim 14, wherein the morphological feature is the sperm's head, and wherein said measurements include a head size and shape, acrosome area, nucleus area, vacuole number, vacuole area, and wherein said acrosome area and nucleus area are measured under a high magnification objective by detecting regions with different pixel intensities on the sperm head, and wherein said vacuole number and vacuole area are detected by detecting holes on the sperm head in binarized high magnification images.

19. The method of claim 18, wherein said detecting the holes is achieved by using a Hough transform or template matching.

20. A system comprising:
(a) a host computer;
(b) a microscope;
(c) a motorized positioner, which controls a motion of a container for containing motile microscopic specimens, the motorized positioner being operationally connected or linked through wire connection or wireless connection to the host computer;
(d) at least a first objective magnification lens and a second objective magnification lens, the second objective magnification lens having a greater magnification power than the first objective magnification lens, the first and second magnification lenses being mounted on a motorized objective nosepiece;
(e) a motorized objective nosepiece, which controls a switch of first and second objectives magnification lenses with different magnifications, and is operationally connected or linked or linked through wire connection or wireless connection to the host computer;
(f) an image acquiring unit mounted on the microscope operationally connected or linked through wire connection or wireless connection to the host computer; and
(g) a focus adjusting motor, which may be mounted on a focus adjusting knob of the microscope and be operationally connected or linked through wire connection or wireless connection to the host computer;
wherein the host computer comprises a computer program comprising instructions to execute the steps of the method according to claim 1.

* * * * *